United States Patent
Ponce et al.

(10) Patent No.: US 7,467,420 B2
(45) Date of Patent: Dec. 23, 2008

(54) APPLICATOR GLOVE FOR APPLICATION OF STAINING COMPOSITIONS AND SELF-TANNING KIT INCLUDING SAME

(76) Inventors: Laura Ponce, 210 E. Broadway, #H508, New York, NY (US) 10002; Peter Weiss, 300 E. 34th St., New York, NY (US) 10016

(*) Notice: Subject to any disclaimer, the term of this patent is extended or adjusted under 35 U.S.C. 154(b) by 395 days.

(21) Appl. No.: 11/191,372

(22) Filed: Jul. 26, 2005

(65) Prior Publication Data
US 2007/0025932 A1 Feb. 1, 2007

(51) Int. Cl.
*A41D 19/00* (2006.01)

(52) U.S. Cl. .................. 2/159; 2/57; 2/161.1; 2/167; 2/161.3; 2/161.6; 2/161.7; 2/164; 442/182; 442/312; 442/197; 442/306; 442/310

(58) Field of Classification Search ............ 2/159, 2/57, 161.1, 167, 161.6, 161.7, 164; 442/182, 442/312, 197, 306, 310
See application file for complete search history.

(56) References Cited

U.S. PATENT DOCUMENTS

| | | | |
|---|---|---|---|
| 4,515,773 A | 5/1985 | Herlihy | |
| 4,714,609 A | 12/1987 | Carden | |
| 4,783,332 A | 11/1988 | Schreuder | |
| 4,968,497 A | 11/1990 | Wolfram et al. | |
| 5,061,480 A | 10/1991 | Marchese et al. | |
| 5,070,540 A * | 12/1991 | Bettcher et al. | 2/2.5 |
| 5,078,160 A | 1/1992 | Carbonnier | |
| RE33,845 E | 3/1992 | Schreuder | |
| 5,167,038 A * | 12/1992 | Rinehart | 2/164 |
| 5,252,322 A | 10/1993 | Stoner et al. | |
| 5,503,824 A | 4/1996 | Lentini et al. | |
| 5,514,367 A | 5/1996 | Lentini et al. | |
| 5,566,405 A * | 10/1996 | Masley | 2/169 |
| 5,698,184 A | 12/1997 | Pickart | |
| 5,705,145 A | 1/1998 | Miklean et al. | |
| 5,968,533 A | 10/1999 | Porter et al. | |
| 5,972,360 A | 10/1999 | Braun | |
| 6,026,513 A * | 2/2000 | Sima | 2/163 |
| 6,401,250 B1 * | 6/2002 | McNabb | 2/78.2 |
| 6,645,474 B1 | 11/2003 | Galdi et al. | |
| 6,723,306 B2 | 4/2004 | Gueret | |
| 6,962,064 B1 * | 11/2005 | Hardee et al. | 66/174 |
| 2005/0111898 A1 * | 5/2005 | Barton et al. | 401/7 |

* cited by examiner

*Primary Examiner*—Gary L Welch
*Assistant Examiner*—Alissa J Tompkins
(74) *Attorney, Agent, or Firm*—McHale & Slavin, P.A.

(57) ABSTRACT

A kit for application of self-tanning preparations includes a self-tanning composition and an application glove for applying the composition to the skin which is constructed from fabric including microfibers of 1 denier or less. The inner surface of the glove has a liner of an impermeable flexible material adhered thereto. The microfiber fabric can be knit or woven, and can be cellulosic fiber, polyester or other synthetic fiber, or a combination of mechanical or intimate blends. In a preferred embodiment, the microfiber fabric is 85% polyester and 15% spandex, with the technical front including polyester microfiber yarn of 1 denier or less. The technical front of the fabric forms the application surface of the glove. The kit can include a cleansing/exfoliating composition, at least one disposable plastic glove for handling the application glove after use, a disposable tray for receiving the glove after use and a moisturizing preparation for the skin.

13 Claims, 2 Drawing Sheets

APPLICATOR GLOVE FOR APPLICATION OF STAINING COMPOSITIONS AND SELF-TANNING KIT INCLUDING SAME

FIELD OF THE INVENTION

The present invention relates to the application of self-tanning agents to the skin, and more particularly to a novel kit having an improved applicator glove which protects the palms of the hands and ensures even coverage.

BACKGROUND OF THE INVENTION

Tanned skin is viewed as healthy and vital, and the acquisition of a tan is seen by many as a part of an essential beauty regimen to achieve an attractive appearance. However, medical science has demonstrated the dangers of exposure to the sun, particularly UVA and UVB radiation exposure. A spike in the frequency of skin cancers (such as basal cell carcinoma, squamous cell carcinoma and malignant melanoma) can be directly attributed to society's growing emphasis on sun-worshiping. It is also well established that sun exposure can accelerate the aging process of the skin, causing premature wrinkling, discoloration, and loss of tone.

In order to satisfy the public's desire for a healthy, tanned appearance, topical self-tanning preparations have been developed which give the skin a tanned appearance. The self-tanning preparations work by staining or coloring the skin, thus allowing one to impart a bronze color to human skin without exposing the skin to natural or artificial sunlight. Self-tanners are available in liquid, cream, mouse, or gel form which can be applied with the hands.

Self-tanning compositions usually contain one or more self-tanning agents, the most common of which is dihydroxyacetone ("DHA" 1,3-dihydroxy-2-propanone). DHA works through interactions between its hydroxy groups and the amino groups of amino acids and peptides naturally occurring in the skin. These reactions lead to the formation of brown pigments in the skin, thereby giving it an appearance similar to that of a naturally obtained tan. DHA is usually suspended in a water in oil emulsion.

Early self-tanning products were generally unsatisfactory because they tended to turn the skin an unnatural orange color. The self-tanning products currently commercially available are vastly improved over earlier versions in that they can deliver a natural-looking color that appears to be a genuine suntan. However, even with these improved products, uneven application will result in tell-tale streaks and discolorations. Since the color is designed to last for several days, mistakes in application cannot be readily corrected.

Self-tanning preparations which do not contain oil-color the skin more quickly, however such preparations do not spread evenly on, the skin. A water-based DHA solution is in many ways preferable to an oil-based, however such a solution has such a low viscosity that it often drips and causes streaks in the final result. An effective applicator means for aqueous DHA solutions having sufficient absorption properties to deliver an even application would therefore be highly desirable.

When applying self tanning preparations, it is important to shield the hands from the preparations, since darkened palms and fingers are unnatural and an undesirable result. This need is addressed in the prior art in Gueret, U.S. Pat. No. 6,723, 306, which discloses a self-adhering lotion applicator device for adhesive attachment to the hand. The pad is mitten-shaped, and has an adhesive surface and a lotion applicator surface. The Gueret pad is effective for shielding the hand, however in use it would be cumbersome and would greatly limit the wearer's dexterity when applying lotion since the fingers cannot be independently moved.

It is known in the art to utilize plastic or rubber gloves when applying self-tanning compositions, however plastics and the like do not yield optimum results. Since the tanning product is usually unevenly distributed on the surface of the plastic or rubber glove, the application is uneven, and streaks can easily result. Therefore, what is needed is an easy to use application device of a suitably absorbent material which provides coverage quality superior to that provided by a plastic or rubber glove.

The present invention utilizes a novel tanning composition application article comprised of microfiber material. The unique properties of the microfiber material provide a self-tanning composition applicator having absorbent properties which make it superior to all prior art methods.

Microfibers are very fine fibers compared to more conventional textile fibers. For example, microfibers are half the diameter of a silk fiber, one-third the diameter of cotton, one quarter the diameter of fine wood, and one hundred times finer than human hair. Microfibers are finer than any fibers occurring in nature. In order to be called a "microfiber," the fiber must be less than one denier. "Denier" is a weight per unit measure of any linear material defined as the number of unit weights of 0.05 grams per 450-meter length. This is numerically equal to the weight in grams of a 9000-meter length of fiber or yarn. The term defines the diameter or fineness of a continuous or filament fiber such as silk or man-made fibers, with low numbers representing finer sizes and the higher number coarser sizes.

The increasing popularity of self-tanning preparations has created a need for an improved means of applying self-tanning preparations to the skin, and the present invention addresses this need by utilizing microfiber materials in combination with spandex to create a novel one-size-fits-all applicator glove which has sufficient absorbency for even application of the self-tanning product.

SUMMARY OF THE INVENTION

Accordingly, it is an objective of the instant invention to provide a kit for the application of self-tanning preparations which includes a self-tanning product in combination with a novel applicator glove.

It is another objective of the instant invention to provide a novel applicator glove which has superior absorption properties and imparts an even application of product while protecting the hands from color.

It is a further objective of the instant invention to provide an applicator glove for self-tanning preparations which is constructed from microfiber material which provides an application superior to that of prior art plastic gloves.

It is still another objective of the instant invention to provide an applicator glove for self-tanning preparations constructed from knit microfiber fabric having a technical front primarily comprising of microfibers of about 1 denier or less and a technical back primarily comprising less absorbent fibers.

It is still another objective of the instant invention to provide an applicator glove for self-tanning preparations which is constructed from microfiber material which includes spandex yard in order to provide elastic properties to create a snug-fitting one-size-fits-all glove.

It is yet another objective of the present invention to provide a kit for the application of self-tanning preparations which also includes a cleansing/exfoliating preparation to be used prior to the application of the self-tanning preparation.

It is a still a further objective of the invention to provide a kit for the application of self-tanning preparations which also includes an emollient preparation to be used after to the application of the self-tanning preparation.

It is yet another objective of the instant invention to provide an applicator glove for self-tanning preparations which is constructed from microfiber material and can be effectively used with both oil-based and water-based self-tanning preparations.

It is a further objective of the present invention to provide an applicator glove for self-tanning preparations constructed from microfiber material which has an inner surface with an impermeable liner adjacent thereto to protect the hands.

It is still another objective of the present invention to provide an applicator glove for self-tanning preparations which can be used with self-tanners in foam, mouse, gel, or cream form.

In accordance with the above objectives, an application glove for self-tanning preparations is provided which is constructed from a microfiber fabric having a technical front and a technical back wherein at least the technical front includes microfibers of about 1 denier, or less than 1 denier, with the technical front forming the application surface of the glove. In preferred embodiment, the microfiber glove is knit from two dissimilar yarns to provide a technical front consisting in large part of microfibers of about 1 denier or less, and a technical back of a less absorbent material such as a polyester/spandex blend. The microfibers on the technical front form the contact surface which for application of the self-tanner to the skin. The application glove has an inner liner of impermeable flexible material which provides a barrier layer. The microfiber can be cellulosic fiber polyester or other synthetic (petroleum-based) fiber, or cellulosic fiber in combination with synthetic fibers, either in mechanical or intimate blends. In a preferred embodiment, the microfiber fabric is 85% polyester and 15% spandex. In an alternative embodiment, the microfiber comprises polyester and polyamide fibers in combination, and the microfiber is subjected to a splitting process wherein the polyester is split from the polyamide. The microfiber fabric can be interlock, knit, woven, warp knitted, rochelle knit, or tricot.

A kit for application of self-tanning preparations to human skin comprises a self-tanning composition comprising an agent for imparting an artificial tan to human skin suspended in a pharmacologically acceptable carrier, a sealable container for containing and dispensing the self-tanning composition, and an application glove constructed from microfiber fabric. The microfiber fabric has a technical front forming the application surface and a technical back forming an inner surface. The technical front comprises in large part microfibers of about 1 denier or less, with the technical back consisting primarily of non-absorbent fibers. The inner surface of the application glove liner having impermeable flexible material adjacent or adhered thereto to provide a barrier layer to protect the hands. The kit can further comprise an emollient preparation for topical application to human skin, a skin cleansing/exfoliating composition, at least one disposable plastic glove for handling the application glove after use, and a disposable tray for receiving the glove after use. The kit can also include a detergent composition for washing the application glove. In use, the skin is first cleansed with the cleansing/exfoliating composition, and then the application glove is used to apply the self-tanning preparation. The emollient composition is applied afterward and serves to prolong the color imparted by the self-tanning composition.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention. The scope of the invention is defined by the claims appended hereto.

Figure 1:
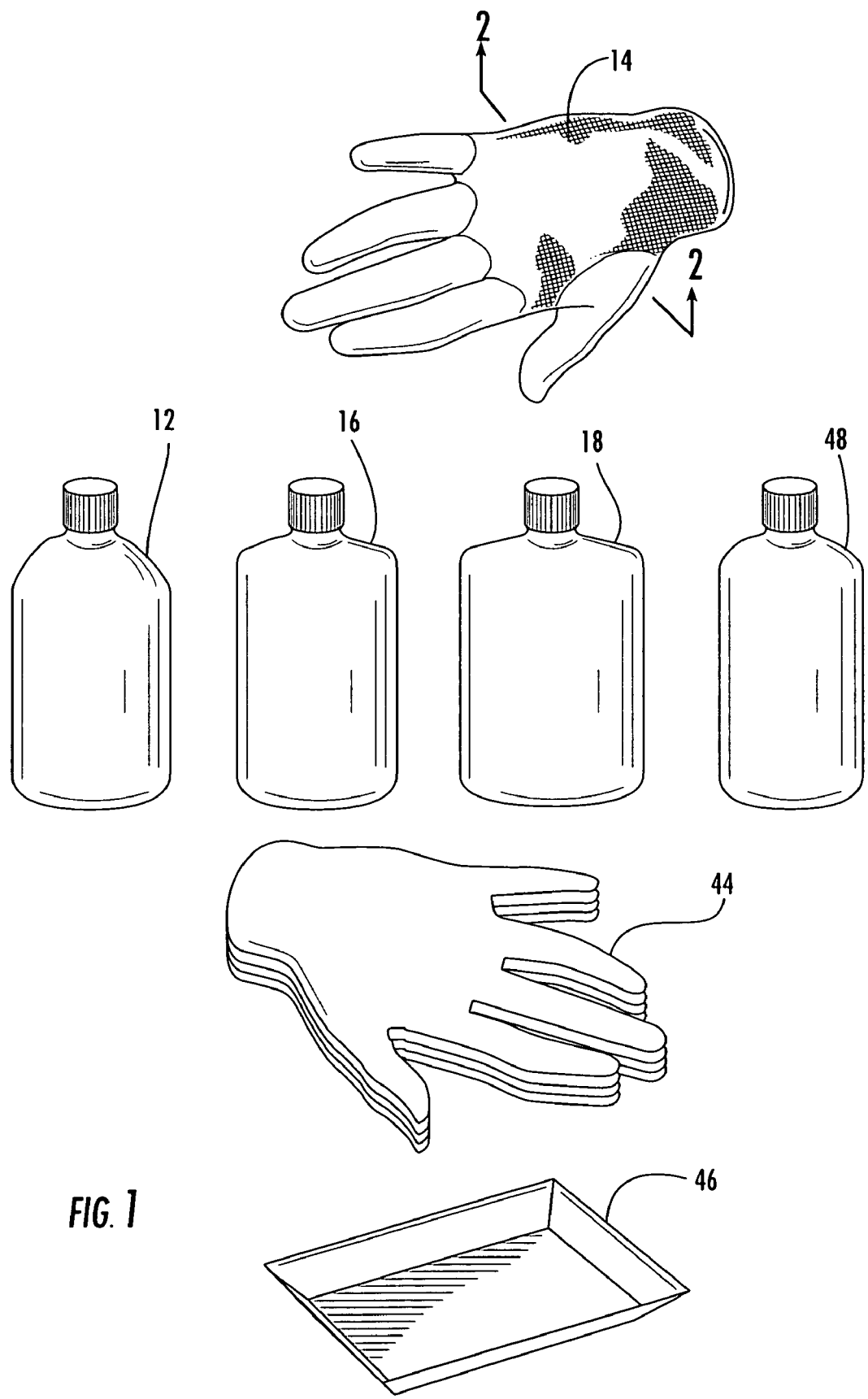
FIG. 1 illustrates the elements of a kit for applying a self-tanning composition to the skin according to a preferred embodiment of the invention.

FIG. 1 illustrates the elements of the inventive kit 10 according to a preferred embodiment. The kit includes a self-tanning composition 12 in a suitable container and an application glove 14. Other elements of the kit 10 can include a cleansing/exfoliant preparation 16 and an emollient preparation 18, both in suitable containers.

The self-tanning composition 12 can be any suitable product which includes a self-tanning agent. The self-tanning agent can be dihydroxyacetone ("DHA") $CH_2OHC(O)CH_2OH$. Other suitable self-tanning agents include, without limitation, methyl glyoxal, glycerol aldehyde, erythrulose, alloxan, 2,3-dihydroxysuccindialdehyde, 2,3 dimethoxysuccindialdehyde, 2-amino-3-hydroxysuccindialdehyde, and 2-benzylamino-3-2-amino-3-hydroxysuccindialdehyde. The self-tanning agent is suspended in any suitable pharmacologically acceptable carrier, which can be a water-in-oil emulsion or a water-based substrate. The self-tanning composition 12 can be in foam, gel, mouse or cream form, with the type of container selected to be appropriate to the type of composition.

The application glove 14 of the invention has an outer layer of a flexible, skin-like material which will absorb the product and spread it evenly. In the preferred embodiment, the application glove 14 is constructed from microfiber fabric including microfibers of 1.1 denier or less. In the preferred embodiment, the microfibers are about 1 denier or less than 1 denier. The microfiber can be cellulosic fiber, polyester or other synthetic (petroleum-based) fiber, or cellulosic fiber in combination with synthetic fibers, either in mechanical or intimate blends. The microfiber fabric can be knit or woven. Suitable knitted constructions include, but are not limited to, single knit, double knit, warp knit, rochelle knit, or tricot. As will be discussed in detail hereinafter, the glove includes an inner barrier layer of a flexible impermeable material to protect the hand.

The glove 14 can be manufactured from cellulosic fibers, such as cotton, or synthetic petrochemical fibers, such as polyester. The fibers may be used in 100% form, or from blended fibers, including cellulosic fiber in combination with synthetic fibers, either in mechanical or intimate blends. Spandex (such as Lycra® manufactured by DuPont), monofilament, rubber, or elastomerics may be utilized or introduced to the fabric construct to create a "one size fits all"

property. Jersey constructions and interlock knits which are designed to have mechanical stretch in both length and width can be used for greater comfort and fit.

In the preferred embodiment, the glove fabric is a basic single knit jersey including polyester microfiber. The knit microfiber fabric includes a spandex component to provide sufficient elasticity to the fabric to create a one-size-fits-all applicator glove. The spandex component advantageously allows the applicator glove 14 to be constructed to fit snugly on the hand. The microfiber/spandex applicator glove 14 of the invention allows the user greater dexterity and touch sensitivity than prior art plastic gloves.

The fabric for the preferred embodiment of the glove 14 is knit from two dissimilar yarns, the first being a polyester microfiber of about 1 denier or less, and the second a polyester/spandex blend fiber which can be greater than 1 denier. In manufacturing the fabric of the glove of the invention, a knitting process is used to create a knitted fabric having a technical front consisting of mostly of polyester microfibers, and a technical back consisting of mostly polyester spandex fibers. The surface of the technical front therefore primarily includes the polyester microfibers, which forms the contact/application surface of the glove 14. It will be appreciated by those skilled in the art that in the fabric produced in the knitting process the polyester microfibers and the polyester/spandex fibers are not distributed in discrete layers in the fabric. However, in the microfiber fabric of the invention the fibers of one yarn are predominantly located on the technical front of the fabric and the other yarn fibers are predominantly located on the technical back of the fabric.

This dual-sided construction of the knitted fabric provides numerous advantages. Since microfiber is relatively expensive to manufacture, and therefore more costly, it is more economical to combine the microfibers with inexpensive non-microfiber yarns in a construction which concentrates the microfibers on one application side. It is also more advantageous to have an application layer, i.e. the technical front comprising microfibers, which is much more absorbent than the technical back. In this way the self-tanning preparation is maintained primarily on the surface during the application process where it can be applied to the skin and is not absorbed into the glove.

Figure 2:
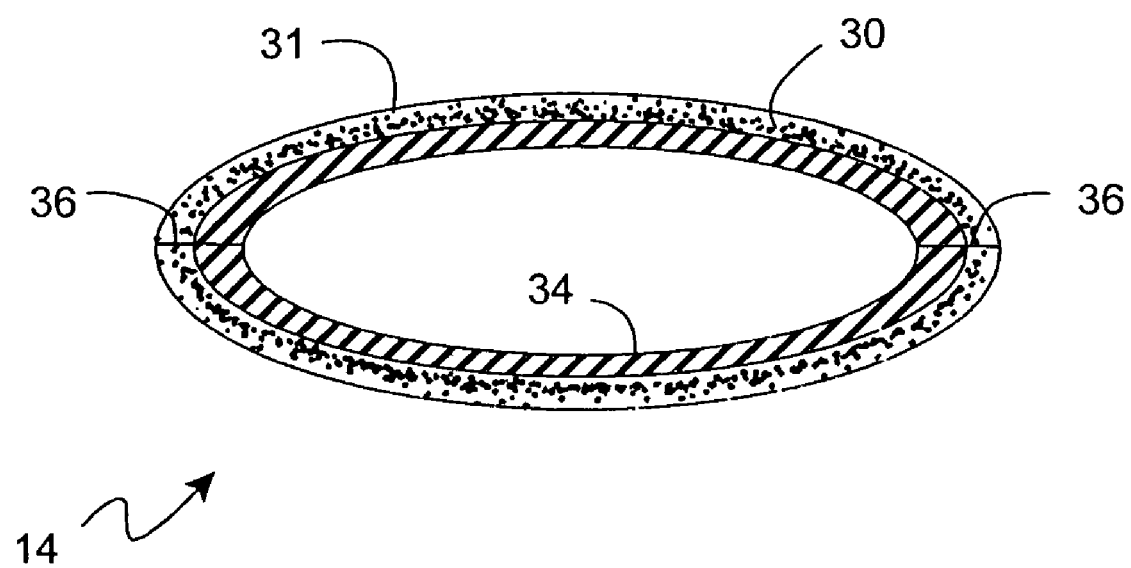
FIG. 2 is a cross-sectional view of the application glove of the invention taken along the line 2-2' in FIG. 1.

A representative cross-sectional view of the glove 14 is shown in FIG. 2 (greatly enlarged to show detail). The glove 14 is constructed from a microfiber fabric 30 having a technical front and a technical back, with the technical front of the fabric forming the outer surface 31 (or application surface) of the glove 14. As discussed above, the material is preferably knit so that the technical front consists in large part of the microfiber yarn, and the technical consists in large part of a spandex/polyester blend In the preferred embodiment, the glove 14 has two discrete layers, an outer application layer consisting of the microfiber fabric 30 and a second inner barrier layer in the form of liner 34 which prevents the stain from reaching the hands. The liner 34 is positioned in juxtaposed relation to the application layer 34, and can be adhered to the microfiber fabric 30 or otherwise sewn into the seams 36 of the glove so as to be adjacent to the microfiber fabric 30. The liner 34 can be any suitable liquid impermeable material such as natural or synthetic rubber, plastic, PVC, latex or polyester. In the preferred embodiment, the liner 34 is coextensive with the microfiber fabric 30 so that it extends over the entire technical back of the fabric 30. However, for applications where the glove 14 is not fully submersed in a substance, the glove 14 can be constructed so that the liner 34 only shields the palmar section and fingers of the hand in order to provide a more comfortable fit. The liner 34 can be attached to the microfiber fabric using any suitable means, including, but not limited to, stitching, heat sealing with no stitches, laser cutting, adhesives, spray laminating, and heat-sealed stitches.

The glove 14 is described herein as being for the application of self-tanning preparations, however the glove 14 constructed in accordance with the principles of the invention can be used in combination with a variety of products, particularly staining products, for application of the product to a surface. For example, the glove 14 can be used to apply wood stains, automobile polish, silver polish, and furniture oils. The body of the glove 14 can be made in fibers and constructions that are specific to the end use.

A suitable microfiber fabric for the application glove 14 is Ultrasuede®, a nonwoven synthetic suede-like material which is described in U.S. Pat. No. 3,705,226 for "Artificial Leather and a Method for Manufacturing the Same." The content of this patent is hereby incorporated by reference. Ultrasuede® is manufactured by Toray Ultrasuede (America), Inc.

In a knitted construction, first and second yarns of different compositions can be knit together to provide a technical front consisting of the first yarn and a technical back consisting of the second yarn. To provide an application glove 14 which is economical to produce, a first microfiber yarn of less than 1 denier can be knit with an inexpensive second yarn which can be greater than 1 denier (e.g. a polyester) to create a fabric with a technical front consisting of the microfiber yarn. The fabric thus produced can be used to provide an application glove with an application surface consisting of microfiber yarn of less than 1 denier, with the technical back of the fabric consisting of non-microfiber yarn. In the preferred embodiment, the first yarn consists of 75 denier, 75 filament polyester microfiber (1 denier per filament) and 40 denier 4 filament spandex (10 denier per filament), and the second yarn consists of 70 denier 34 filament polyester fibers (about 2 denier per filament). The fabric preferably consists of approximately 45% of 75 denier, 75 filament polyester microfiber, approximately 15% 40 denier 4 filament spandex and approximately 40% 70 denier 34 filament polyester fibers, thus providing a fabric composition of approximately 85% polyester and 15% spandex.

The fabric of the preferred embodiment can be constructed according to the following specification:

1. 11.5-12 oz/linear yard (±10%)
2. 58-60 inches (±10%)
3. 70 denier 34 filament @ 40%, 75 denier, 75 filament polyester micro-fiber @ 45%, 40 denier filament Spandex @ 15% (±10%)
4. 1 denier per filament microfiber (±10%)
5. 10 denier 4 filament relaxed (±10%)
6. 2 bar Tricot
7. 28 cut (±10%)

The finishing for the fabric can include denier reduction chemicals during the dying and aqueous processing. Surface or face finishing can include caustic reduction, napping, brushing, sueding, and shearing can be used to increase surface filament count to increase surface acceptance of fluids.

An alternative embodiment of the glove 14 for use with water-based or other low-viscosity solutions is made from microfiber fabric having polyester and polyamide fibers in combination, preferably 50% polyester and 50% polyamide. To create a highly absorbent fabric, the microfiber is subjected to a "splitting" process to split the polyester from the polyamide. The split fiber allows the polyamide to pull liquid into the fiber, thereby creating a wicking action through capillary flow. The glove 14 thus formed is ideal for use with aqueous solutions, such as DHA suspended in an oil-free substrate, as well as other low viscosity solutions. The solution is immediately absorbed into the glove 14 so it can be applied to a surface with minimal dripping.

The human epidermis is continually generating new skin cells and shedding older, dead skin cells. When skin is subjected to the self-tanning agents, it can happen that the newer skin cells can absorb the color differently than older cells. To obtain a even coloration and optimal results, it is advantageous to slough off the dead skin just prior to applying the self-tanning preparation 12. The kit 10 of the invention therefore includes a cleansing/exfoliating composition 16 in a suitable container. The cleansing/exfoliating composition 16 can be any suitable commercially available product. To keep the skin moisturized after application of the self-tanning composition 12, the kit 10 can also include an emollient composition 18 in a suitable container. Application of the emollient compositing 18 to the skin helps lengthen the life of the color application by moisturizing the skin to prevent skin flaking.

As shown in FIG. 1, the kit 10 can also include at least one disposable plastic glove 44. The plastic glove 44 can be worn on the hand opposite the application hand in order to remove the sodden glove 14 from the application hand after the self-tanner 12 is applied. In a preferred embodiment, the kit 10 can include a plurality of disposable plastic gloves 44 for multiple applications. The kit 10 can also include a disposable tray 46 for placement of the glove 14 after application to minimize cleanup. The kit 10 can also include a detergent composition 48 for in a suitable container for washing the glove. The detergent composition 48 can be specific to the type of microfiber used.

To use the kit of the invention the apply self-tanning composition 12, the user can first cleanse the skin with the cleansing/exfoliating composition 16. The microfiber application glove is then donned on the application hand, and is used to apply the self-tanning preparation 12. The glove 14 can be removed using a plastic glove 44 worn on the opposite hand, and placed in the tray 45 to minimize cleanup. The emollient composition 18 can be applied after application. The glove 14 is re-usable, and can be machine laundered or hand-washed for future applications.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

We claim:

1. A liquid impermeable glove construction comprising in combination:

a palm portion including closed finger portions, said palm portion comprising an elastic microfiber fabric layer and a liquid impermeable elastic liner layer extending coextensively with respect to each other, said liner layer adhesively secured to said fabric layer so that said fabric layer and said liner layer stretch in unison;

a back portion including closed finger portions, said back portion comprising a liquid impermeable elastic liner layer wherein said back portion includes a microfiber layer extending coextensively with respect to said barrier layer, said barrier layer adhered to said fabric layer for stretching in unison therewith;

said palm portion sealed around a perimeter thereof to a perimeter of said back portion to form a liquid impermeable seal, whereby said liquid impermeable glove is adapted to enclose the hand and fingers of a user.

2. The liquid impermeable glove of claim 1 wherein said microfiber fabric has a knitted construction.

3. The liquid impermeable glove of claim 2, wherein said microfiber comprises polyester.

4. The liquid impermeable glove of claim 3, wherein said microfiber fabric comprises approximately 85% polyester and 15% spandex in a knitted construction.

5. The liquid impermeable glove of claim 2, wherein said microfiber fabric is knit from a first yarn and a second yarn to provide a technical front consisting primarily of said first yarn and a technical back consisting primarily of said second yarn.

6. The liquid impermeable glove of claim 5 wherein said technical front is more absorbent than said technical back.

7. The liquid impermeable glove of claim 5 wherein said technical front includes increased wickability with respect to said technical back.

8. The liquid impermeable glove of claim 5 wherein said technical front includes a face surface that has been subjected to a fiber splitting process.

9. The liquid impermeable glove of claim 8 wherein said fiber splitting process is selected from the group consisting of caustic reduction, napping, brushing, sueding and shearing.

10. The liquid impermeable glove of claim 5, wherein said microfiber fabric is knit from a first yarn including microfiber of about one denier or less and a second yarn greater than one denier to provide a technical front consisting primarily of said first yarn and a technical back consisting primarily of said second yarn.

11. The liquid impermeable glove of claim 10, wherein said first yarn comprises 75 denier 75 filament polyester microfiber, and said second yarn comprises 70 denier 34 filament polyester fibers and 40 denier 4 filament spandex.

12. The liquid impermeable glove of claim 1 wherein said microfiber fabric has a knitted construction.

13. The liquid impermeable glove of claim 1, wherein said liner is formed from material selected from the group consisting of natural rubber, synthetic rubber, plastic, PVC, latex and polyester.

\* \* \* \* \*